United States Patent
Bryant et al.

Patent Number: 6,110,942
Date of Patent: Aug. 29, 2000

[54] METHOD FOR MINIMIZING THE UTEROTROPHIC EFFECT OF DROLOXIFENE

[75] Inventors: Henry Uhlman Bryant; Jeffrey Alan Dodge, both of Indianapolis, Ind.

[73] Assignee: Eli Lilly and Company, Indianapolis, Ind.

[21] Appl. No.: 08/867,058

[22] Filed: Jun. 2, 1997

Related U.S. Application Data

[60] Provisional application No. 60/019,806, Jun. 17, 1996, and provisional application No. 60/022,879, Aug. 20, 1996.

[51] Int. Cl.[7] .................. A61K 31/445; A61K 31/135
[52] U.S. Cl. ................................. 514/324; 514/648
[58] Field of Search .................... 514/648, 324

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 546/237 |
| 4,656,187 | 4/1987 | Black et al. | 514/648 |
| 5,047,431 | 9/1991 | Schickaneder et al. | 514/648 |
| 5,254,594 | 10/1993 | Kazuaki et al. | 514/648 |
| 5,384,332 | 1/1995 | Fontana | 514/648 |
| 5,550,150 | 8/1996 | Fontana | 514/324 |
| 5,554,526 | 9/1996 | Cullinan | 514/324 |
| 5,604,248 | 2/1997 | Bryant et al. | 514/324 |

OTHER PUBLICATIONS

Fisher, et al., *JNCI*, 86(7) :527–537, (1994).
Malfetano, J. H., *Gynecol. Oncol.*, 37:82–84 (1990).
Kirkland, J. L., et. al., *Molecular Pharmacology*, 43:709–714, (1993).
Wakeling, et. al., *J. Steroid Biochem.*, 20(1) :111–120, (1984).
Jordan, V. C., et. al., *Ann. N.Y. Acad. Sci.*, 622:439–446, (1991).
Fuchs–Young, et. al., *Breast Cancer Res. Treatment*, 32:78.
Black, L.J., et. al., *Life Sciences*, 32:1031–1036, (1982).

*Primary Examiner*—Jerome D. Goldberg
*Attorney, Agent, or Firm*—William R. Boudreaux; James J. Sales

[57] ABSTRACT

The present invention provides a method of minimizing the uterotrophic effect of a compound of formula II

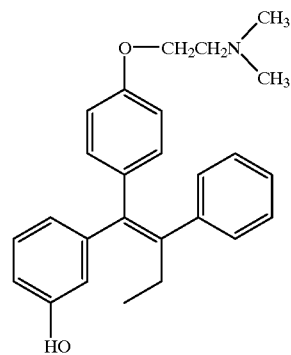

(II)

or a pharmaceutically acceptable salt or solvate thereof, comprising concurrently or sequentially administering a compound of formula I

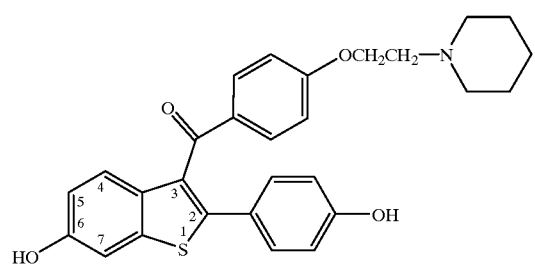

(I)

or pharmaceutically acceptable salt or solvate thereof.

6 Claims, No Drawings

METHOD FOR MINIMIZING THE UTEROTROPHIC EFFECT OF DROLOXIFENE

This application claims the benefit of U.S. Provisional Applications Ser. Nos. 60/019,806, filed Jun. 17, 1996 and 60/022,879 filed Aug. 20, 1996.

BACKGROUND OF THE INVENTION

Droloxifene, 1-[4'-dimethylaminoethoxy)phenyl]-1-(3'-hydroxyphenyl)-2-phenylbut-1-ene, represented by the structure

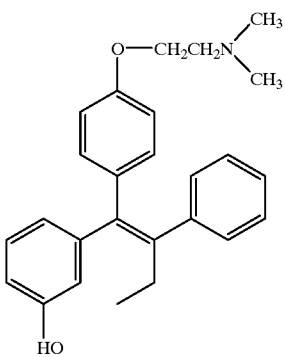

(II)

is a known compound which is currently in phase II and III human studies for osteoporosis and breast cancer. Although all indications are that droloxifene has certain levels of efficaciousness in the treatment/prevention of these diseases, it is known to induce certain uterotrophic effects which may be detrimental to the patient. (Bryant et al., *Soc. Gynecol. Invest.* 3, 152A (1996)). It, therefore, would be beneficial if a pharmaceutical agent was available which would not affect the benefit which droloxifene may provide while minimizing or eliminating any undesired uterotrophic effect.

Thus, the present invention provides a method of minimizing the uterotrophic effect of droloxifene via the concurrent or sequential administration of certain nuclear regulating benzothiophene pharmaceutical agents.

SUMMARY OF THE INVENTION

The present invention provides a method of minimizing the uterotrophic effect of a compound of formula II

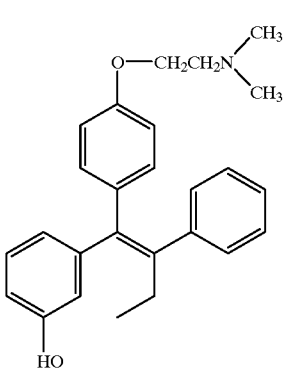

(II)

or a pharmaceutically acceptable salt or solvate thereof, wherein said formula II compound is administered to a woman, comprising concurrently or sequentially administering to said woman a compound of formula I

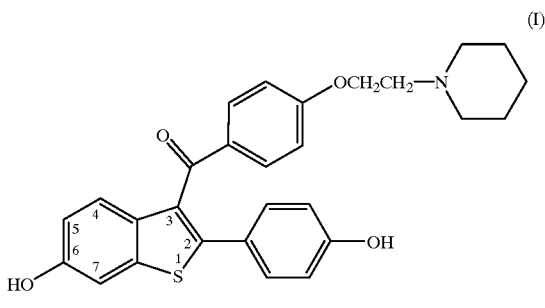

(I)

or a pharmaceutically acceptable salt or solvate thereof.

Also provided are pharmaceutical compositions comprising a compound of formula I and a compound of formula II together with one or more pharmaceutically acceptable carriers, excipients or diluents.

DETAILED DESCRIPTION OF THE INVENTION

The present invention concerns the discovery that a compound of formula I is useful for minimizing the uterotrophic effect of a compound of formula II.

Raloxifene, the hydrochloride salt of a compound of formula I, is a nuclear regulatory molecule. Raloxifene has been shown to bind to estrogen receptors and originally was demonstrated to have antiestrogenic activity because it blocked the ability of estrogen to activate uterine tissue and estrogen dependent breast cancers. Indeed, raloxifene does block the action of estrogen in some cells; however in other cell types, raloxifene activates the same genes as estrogen activates and displays the same pharmacology, e.g., prevention of estrogen deficiency induced bone loss; lowering serum cholesterol. As a result, raloxifene has been referred to as a tissue selective antiestrogen with mixed agonist-antagonist properties. Therefore, although raloxifene and estrogen generally utilize and compete for the same receptors, the pharmacological outcome of administration of the two agents is not easily predicted, and is distinct to each.

A compound of formula I used in the methods and pharmaceutical compositions of the present invention may be made according to established procedures, such as those detailed in U.S. Pat. Nos. 4,133,814, 4,418,068, and 4,380,635, each of which is herein incorporated by reference.

Compounds of formula I form pharmaceutically acceptable acid and base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4- dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts and solvates generally have enhanced solubility characteristics compared to the compound from which they are derived, and thus are often more amenable to formulation as liquids or emulsions.

Compounds of formula II used in the methods and pharmaceutical compositions of the present invention are prepared by established procedures, such as those described in U.S. Pat. Nos. 5,047,431 and 5,254,594, which are herein incorporated by reference. Pharmaceutically acceptable acid addition salts of formula II compounds are prepared via the above-described process. A preferred salt is the citrate salt.

One aspect of the present invention provides a method of minimizing the uterotrophic effect of a compound of formula II, particularly droloxifene, by administering a compound of formula I, particularly raloxifene, to a woman receiving administrations of a formula II compound for the treatment or prevention of breast carcinoma. In this context, "uterotrophic effect" means the proliferation of uterine epithelial cells, which may be a side effect of droloxifene administration to women.

Administration of a formula I compound, particularly raloxifene, minimizes the uterotrophic effect of a concurrently or sequentially administered formula I compound, particularly droloxifene, without affecting the formula II compounds efficacy against breast carcinoma. The term "minimize", or a derivative thereof, includes partial or complete inhibition of the droloxifene-induced uterotrophic effect on uterine epithelial cells.

For the treatment of human breast carcinoma, droloxifene can be administered alone or in combination with other chemotherapeutic agents and/or radiotherapy, as an adjuvant to surgery, or, in certain circumstances, may be considered for use as a chemosuppressive/chemoprophylactic agent. Because each of these administration regimes may present various degrees of risk of uterotrophic side effects, the attending physician is best suited to decide whether the administration of a formula I compound should be concurrent or sequential to the administration of a formula II compound.

When administered sequentially, pharmaceutical formulations of compounds of formulae I and II are prepared by methods known by one of ordinary skill in the art.

When administered concurrently, formula I and formula II compounds may be prepared into pharmaceutical formulations via the above-mentioned known methods, and administered as separate entities. Alternatively, they may be combined to form a pharmaceutical composition of the present invention which comprises an effective amount of a formula I compound and an effective amount of formula II compound, preferably raloxifene and droloxifene, respectively, together with a pharmaceutically acceptable carrier, excipient, or diluent.

As used above and throughout this specification, the term "effective amount" means that dosage of active compound (s) sufficient to provide therapeutic treatment of the specified medical indication.

The term "active compound" as used throughout this specification, refers to a formula I compound, or a pharmaceutically acceptable salt or solvate thereof, and/or a formula II compound, or a pharmaceutically acceptable salt thereof.

For therapeutic treatment of the specified indications, a formula I compound, with or without a formula II compound, may be administered as such, or can be compounded and formulated into pharmaceutical compositions in unit dosage form for parenteral, transdermal, rectal, nasal, intravenous administration or, preferably, oral administration. Such pharmaceutical compositions are prepared in a manner well known in the art and comprise a formula I compound, optionally including a compound of formula II. In making the compositions of the present invention, the active ingredients will usually be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Additionally, compounds of the present composition, particularly formula I compounds, are well suited to formulation as sustained release dosage forms and the like. The formulations can be so construed that they release the active ingredient only or preferably in a particular physiological location, possibly over a period of time. The coatings, envelopes, and protective matrices may be made, for example, from polymeric substances or waxes.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The compositions can additionally include lubricating agents, wetting agents, emulsifying and suspending agents, preserving agents, sweetening agents or flavoring agents. The compositions may be formulated so as to provide quick, sustained, or delayed release of the active ingredient(s) after administration to the patient by employing procedures well known in the art. For oral administration, a compound optionally including a second component compound, can be admixed with carriers and diluents molded into tablets or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient(s). The term "unit dosage form" refers to physically discreet units suitable as unitary dosages for human subjects, each unit containing a predetermined quantity of active ingredients calculated to produce the desired therapeutic effect, in association with the required pharmaceutically acceptable carrier. By "pharmaceutically acceptable", it is meant the carrier, diluent, or excipient must be acceptable with the other ingredients of the formulation and not deleterious to the recipient thereof.

Compounds of formula I, alone or in combination with a pharmaceutical agent of the present invention, generally will be administered in a convenient formulation. The following formulation examples only are illustrative and are not intended to limit the scope of the present invention.

Formulations

Formulation 1: Gelatin Capsules

Hard gelatin capsules are prepared using the following:

| Ingredient | Quantity (mg/capsule) |
| --- | --- |
| Formula I compound | 0.1–1000 |
| Starch, NF | 0–650 |
| Starch flowable powder | 0–650 |
| Silicone fluid 350 centistokes | 0–15 |

Formulation 2: Raloxifene capsule

| Ingredient | Quantity (mg/capsule) |
| --- | --- |
| Raloxifene HCl | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
| --- | --- |
| Raloxifene HCl | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
| --- | --- |
| Raloxifene HCl | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
| --- | --- |
| Raloxifene HCl | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Formula I compound | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 25–1000 mg of a formula I compound are made up as follows:

Formulation 7: Tablets

| Ingredient | Quantity (mg/tablet) |
| --- | --- |
| Formula I compound | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The formula I compound, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 25–1000 mg of medicament per 5 ml dose are made as follows:

Formulation 8: Suspensions

| Ingredient | Quantity (mg/5 ml) |
| --- | --- |
| Formula I compound | 25–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 9: Raloxifene and Droloxifene Capsule

| Ingredient | Quantity (mg/capsule) |
| --- | --- |
| Raloxifene HCl | 200 |
| Droloxifene | 20 |
| Avicel pH 101 | 50 |
| Starch 1500 | 117.50 |
| Silicon Oil | 2 |
| Tween 80 | 0.50 |
| Cab-O-Sil | 0.25 |

Formulation 10: Raloxifene and Droloxifene Capsule

| Ingredient | Quantity (mg/capsule) |
| --- | --- |
| Raloxifene HCl | 200 |
| Droloxifene | 20 |
| Avicel pH 101 | 82.50 |
| Starch 1500 | 90 |
| Silicon Oil | 2 |
| Tween 80 | 0.50 |

Formulation 11: Raloxifene and Droloxifene Tablet

| Ingredient | Quantity (mg/capsule) |
| --- | --- |
| Raloxifene HCl | 200 |
| Droloxifene | 20 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

The particular dosage of a compound of formula I, particularly Raloxifene, required to minimize the uterotrophic effect of a compound of formula II according to this invention will depend upon the severity of the condition, the route of administration, and related factors that will be decided by the attending physician. Generally, accepted and effective daily doses of a formula I compound will be from about 0.1 mg to about 1000 mg/day, and more typically from about 50 mg to about 600 mg/day. Such dosages will be administered to a subject in need of treatment from once to about three times each day, or more often as needed to effectively treat the present indication. Usually, it is preferred to administer a compound of formula I in the form of an acid addition salt, as is customary in the administration of pharmaceuticals bearing a basic group, such as a piperidino ring. It also is advantageous to administer such as a compound by the oral route.

Compounds of formula II, particularly droloxifene, are administered for the treatment of breast carcinoma at dosages and timings which are consistent with those which are well known in the art. Such daily dosages are from about 10 mg/day to 200 mg/day. For use in osteoporosis, the daily dosage may be from about 0.25 mg/day to 400 mg/day. It is preferred to administer a substantial excess of a formula I compound relative to a formula II compound, with a ratio of about 10/1 to 3/1 by weight of a compound of formula I to that of formula II compound.

Test Procedure

General Preparation Procedure

In the examples illustrating the methods, a post-menopausal-type model was used in which the uterine response of different treatments was determined.

It has been found that in ovariectomized rats given droloxifene, raloxifene is capable of antagonizing droloxifene induced elevation of both uterine weight and uterine eosinophil peroxidase activity, particularly when the dose of raloxifene exceeds that of droloxifene by 3 to 10-fold.

Seventy-five day old female Sprague Dawley rats (weight range of 200 to 250 g) were obtained from Charles River Laboratories (Portage, Mich.). The animals were bilaterally ovariectomized (OVX) at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at $22.20°\pm1.7°$ C. with a minimum relative humidity of 40%. The photoperiod in the room was 12 hours light and 12 hours dark.

Dosing Regimen Tissue Collection.

After a one week acclimation period (therefore, two weeks post-OVX) daily dosing with test compound was initiated. The test compounds were given subcutaneously as a suspension in 1.5% carboxymethylcellulose. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Antagonism of Droloxifene Stimulation of Rat uteri by Raloxifene

Data presented in Table 1 below show comparative results among ovariectomized rats, rats treated with Droloxifene and rats treated with the same doses of Droloxifene plus raloxifene.

TABLE 1

| Droloxifene Dose (mg/kg) | Raloxifene Dose (mg/kg) | Uterine Weight (mg) | Uterine Eosinophil Peroxidase Activity (Vmax)[a] |
| --- | --- | --- | --- |
| 0 | 0 | 138 ± 9* | 3 ± 1 |
| 3 | 0 | 171 ± 9* | 53 ± 1 |
| 3 | 0.1 | 183 ± 11* | 96 ± 2 |
| 3 | 1.0 | 187 ± 11* | 68 ± 1 |
| 3 | 10.0 | 142 ± 7† | 7 ± 1 |
| 3 | 30.0 | 132 ± 8† | 5 ± 1 |

[a] = Uterine eosinophil peroxidase activity was determined on pooled uterine samples, therefore, no statistical analyses were performed.
\* = $p < 0.05$ vs. no treatment control
† = $p < 0.05$ vs. Droloxifene only control

What is claimed is:

1. A method of minimizing the uterotrophic effect of a compound of formula II

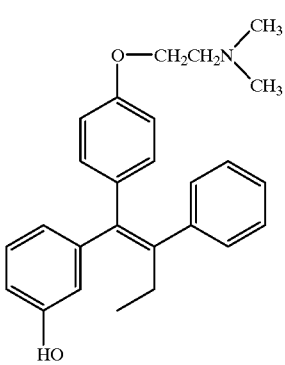

(II)

or a pharmaceutically acceptable salt or solvate thereof, wherein said formula II compound is administered to a woman, comprising concurrently or sequentially administering to said woman an effective amount of a compound of formula I

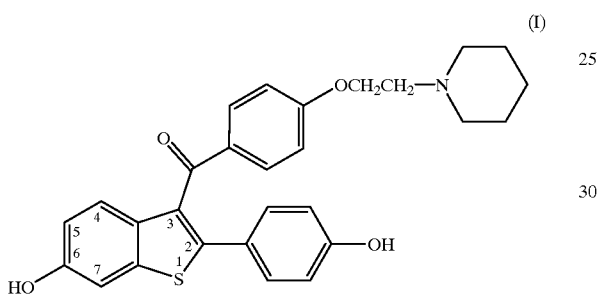

(I)

or a pharmaceutically acceptable salt thereof wherein said formula I compound is administered at a ratio of about 3 to 1 to about 10 to 1, by weight, relative to said formula II compound.

2. A method according to claim 1 wherein said formula II compound is the citrate salt thereof, and the formula I compound is the hydrochloride salt thereof.

3. A method according to claim 1 wherein said formula I compound is administered concurrently to the administration of said formula II compound.

4. A method according to claim 1 wherein said formula I compound is administered sequentially to the administration of said formula II compound.

5. A pharmaceutical composition comprising an effective amount of a compound of formula II

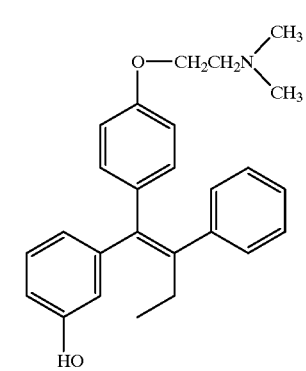

(II)

or a pharmaceutically acceptable salt or solvate thereof, and an effective amount of a compound of formula I

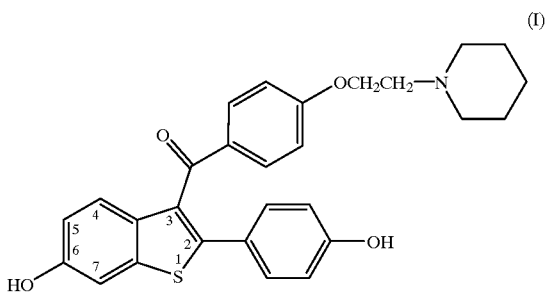

(I)

or pharmaceutically acceptable salt or solvate thereof, optionally together with one or more pharmaceutically acceptable carriers, excipients or diluents wherein said formula I compound is present in said formulation at a ratio of about 3 to 1 to about 10 to 1, by weight, relative to said formula II compound.

6. A pharmaceutical composition according to claim 5 wherein said formula I compound is the hydrochloride salt thereof, and the formula II compound is the citrate salt thereof.

* * * * *